(12) United States Patent
Neumann et al.

(10) Patent No.: US 6,259,767 B1
(45) Date of Patent: Jul. 10, 2001

(54) X-RAY DEVICE INCLUDING AN ADJUSTABLE DIAPHRAGM UNIT

(75) Inventors: Kai Neumann; Klaus Spiess, both of Hamburg; Peter Biermann, Norderstedt, all of (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/411,757

(22) Filed: Oct. 4, 1999

(30) Foreign Application Priority Data

Oct. 5, 1998 (DE) .............................................. 198 45 650

(51) Int. Cl.$^7$ ..................................................... G21K 1/04
(52) U.S. Cl. ............................ 378/151; 378/95; 378/110; 378/112; 378/152
(58) Field of Search ............................ 378/95, 109, 110, 378/111, 112, 151, 152

(56) References Cited

U.S. PATENT DOCUMENTS

| 4,403,337 | * | 9/1983 | Kleinman | 378/95 |
| 4,597,094 | * | 6/1986 | Kleinman | 378/95 |
| 4,955,043 | * | 9/1990 | Nekovar | 378/108 |

* cited by examiner

Primary Examiner—Robert H. Kim
Assistant Examiner—Allen C. Ho
(74) Attorney, Agent, or Firm—John F. Vodopia

(57) ABSTRACT

The invention relates to an X-ray device which operates with only a single image detection device whose format corresponds to the maximum exposure format. In order to facilitate the adjustment of the exposure field for an exposure, a respective set of exposure parameters is stored in a memory for each of the various organs to be imaged; this set includes inter alia an adjustment value for the size of the exposure field for an exposure of the relevant organ. This adjustment value is fetched and the diaphragm unit is automatically controlled in such a manner that the fetched adjustment value is (pre)adjusted.

5 Claims, 2 Drawing Sheets

X-RAY DEVICE INCLUDING AN ADJUSTABLE DIAPHRAGM UNIT

BACKGROUND OF THE INVENTION

1. Field of the Invention

The invention relates to an X-ray device which includes an X-ray imaging apparatus and an X-ray generator for powering an X-ray source which co-operates with the X-ray imaging apparatus and also includes a diaphragm unit which is connected to the X-ray source and includes an adjustable diaphragm aperture in order to preset an exposure field on an X-ray image detection device, the diaphragm aperture being adjustable on the one hand by a drive unit which is controlled by a control system and on the other hand by adjusting means for manual adjustment of the diaphragm aperture.

2. Description of the Related Art

X-ray devices of this kind are known for the formation of Bucky images. Such devices utilize image detection devices in the form of film/foil combinations of various formats which are accommodated in suitably dimensioned cassettes. The examiner then selects the cassette format required for the next X-ray exposure and inserts the cassette into the X-ray device. The X-ray device is provided with a measuring device for measuring the cassette format. The control system then adjusts the diaphragm aperture in dependence on the measured cassette format so that the exposure field corresponds to the cassette format or the format of the film present therein. Such X-ray devices require manual adjustment of the exposure field only if the examiner wishes to constrict the exposure field.

Since recently so-called "digital" X-ray detectors are used as the image detection devices; such detectors include a large number of (for example, 2000×2000) detector elements which are arranged in the form of a matrix, are sensitive to light or X-rays and generate electric signals which are dependent on the X-ray intensity and are processed in the X-ray device. The X-ray device may comprise various imaging units, for example a grid exposure table for forming X-ray images of a supine patient and/or a grid wall stand for forming X-ray images of a standing patient; each of these units is provided with only a single digital detector of this kind whose dimensions, therefore, have to correspond to the largest possible exposure format (for example, 43×43 cm). Automatic adjustment of the diaphragm aperture to the format of this image detector, however, would in most cases require a rather substantial manual restriction of the exposure field, thus complicating the use of such an apparatus.

Citation of a reference herein, or throughout this specification, is not to be construed as an admission that such reference is prior art to the Applicants' invention of the invention subsequently claimed.

SUMMARY OF THE INVENTION

It is an object of the present invention to simplify the use of an X-ray device whose imaging unit (units) has (have) an image detector which has each time only a single (maximum) format. On the basis of an X-ray device of the kind set forth this object is achieved in that there is provided a storage device which co-operates with the control system and in which a respective set of exposure parameters is stored for each of a number of organs, that each set contains, in addition to the exposure parameters for the X-ray detector, an adjustment value for adjusting the exposure field, and that, when an organ is selected, the adjustment value is fetched and the exposure field is adjusted, by way of the control system and the drive unit, in conformity with the adjustment value associated with the selected organ.

The use of a storage device in which respective sets of exposure parameters are stored for various organs has since long been known in the X-ray imaging technique. According to such so-called APR (Anatomically Programmed Radiography) methods, essentially exposure parameters for the X-ray generator, for example the voltage to the X-ray tube, the current through the X-ray tube and the exposure duration, are stored in an organ-dependent manner in order to be fetched and adjusted when the relevant organ is selected.

The invention is based on the recognition of the fact that the size of the exposure field is correlated to the organ or to the body region to be imaged by way of the subsequent X-ray exposure. Therefore, for each organ the size of the required exposure field is stored additionally. The stored adjustment value is fetched when the relevant organ is selected and controls, via the control system and the drive unit, the diaphragm unit in such a manner that the preset exposure field is adjusted. After that, the examiner need only slightly change the exposure field, if at all.

During manual adjustment of the exposure field the examiner is present in the vicinity of the patient who is arranged, for example on a patient table. However, the other adjusting operations, for example selection of an organ, triggering of an X-ray exposure etc., are carried out at a control desk or a workstation which is situated in a room other than that in which the patient is present. In the embodiment wherein the control system is programmed in such a manner that, after actuation of the adjusting means, the manual adjustment of the exposure field is carried out or preserved independently of an adjustment value fetched before or after that, it is ensured that the manual adjustment made for the exposure of the relevant organ is not overwritten by an adjustment value stored for this organ so that it is canceled again. The appropriately programmed control system then consists effectively of a diaphragm controller which is arranged to control the drive unit and the diaphragm unit, as well as of the workstation which controls all components of the X-ray device as well as the overall exposure procedure.

The further embodiment wherein the control system is programmed in such a manner that after an X-ray exposure or a change of a patient to be examined an exposure field adjusted by actuation of the adjusting means is adjusted in conformity with the relevant adjustment value fetched, however, enables a change-over to be made from the manual adjustment to the stored adjustment values when an X-ray exposure or change of patient has taken place after the manual adjustment.

Bucky exposures or exposures on the wall stand are generally executed with a given distance between the X-ray source and the image detector, for example 1.15 m. In that case each exposure field corresponds to a given diaphragm aperture. However, it is often desirable to increase or decrease the distance between the X-ray source and the image detector. Therefore, the further embodiment wherein the distance between the X-ray source and the X-ray image detection device is adjustable, further comprising means for measuring this distance, and wherein the control system is programmed in such a manner that in dependence on the measured distance the diaphragm aperture has a value such that the size of the exposure field on the image detection device assumes its preset value, ensures that when said distance is changed, the diaphragm aperture is also readjusted in such a manner that the desired exposure field is obtained in the plane of the image detector.

The invention can be used with an image detector indicating a flat detector with light-sensitive or X-ray sensitive detector elements which are arranged in the form of a matrix. The invention, however, can in principle be used for all imaging units involving only a single format of the image detector.

BRIEF DESCRIPTION OF THE DRAWING

The invention will be described in detail hereinafter with reference to the drawings. Therein.

DETAILED DESCRIPTION OF THE PREFERRED EMBODIMENT

Figure 1:
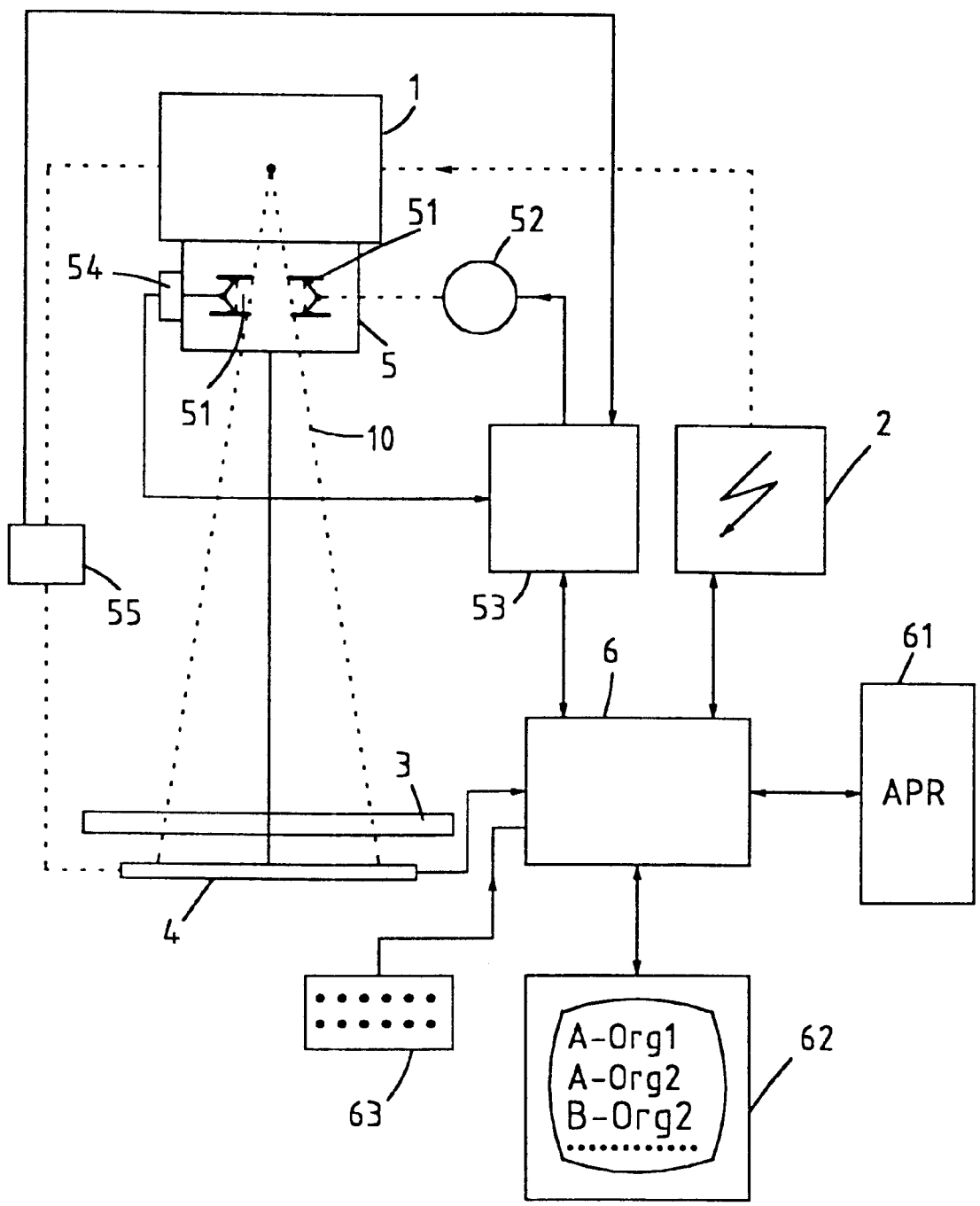
FIG. 1 shows an X-ray device according to the invention.

The X-ray device shown in FIG. 1 includes an X-ray source 1 which is controlled by an X-ray generator 2. The X-ray source is mounted on a stand (not shown) so as to be displaceable at least in the vertical direction. The X-ray device also includes a patient table which is symbolically represented by a table top 3; underneath the table there is arranged a digital image detector 4 with a matrix-like array of detector elements. In addition to the patient table, or instead of the table, there may be provided a grid or Bucky wall stand with such an image detector.

The size of the exposure field formed on the image detector 4 by the X-ray source 1 is adjusted by means of a diaphragm unit 5. The diaphragm aperture, i.e. the angle of aperture of the radiation beam denoted by dashed lines in the plane of drawing, is determined by a first set of collimators 51 which are made of, for example lead and whose edges extend perpendicularly to the plane of drawing of FIG. 1. There is also provided a second set of collimators which, however, is not shown in FIG. 1; these collimators have edges which extend parallel to the plane of drawing and determine the angle of aperture of the radiation beam 10 in the direction perpendicular to the plane of drawing. The diaphragm aperture can be adjusted by means of a motor 52 which is accommodated in the diaphragm unit 5 (unlike the situation shown in the drawing). The motor 52 is controlled by means of a diaphragm controller 53 which co-operates with a workstation 6.

The diaphragm aperture can also be adjusted manually by the examiner while using an adjusting member 54. The actuation of the adjusting member 54 is detected by the diaphragm controller 53. The examiner can check the size of the adjusted exposure field prior to an exposure by using a light localizer (not shown) which is included in the diaphragm unit 5 and produces a light beam which is bounded by the collimators 51 etc. in the same way as the X-ray beam 10 during the exposure. The distance between the X-ray source and the image detector is measured by a measuring device 55 and the measured value is applied to the diaphragm controller 53.

The workstation 6 controls inter alia the diaphragm controller 53 and the X-ray generator 2. To this end it can access a storage device 61 with a data base in which a respective data set is stored for each of a plurality of organs. Each data set contains the optimum exposure parameters for the relevant organ in the normal case; it also includes a value concerning the size of the exposure field to be adjusted. This adjustment value can be applied to the diaphragm controller 53 in order to adjust the exposure field while taking into account the measured distance between the X-ray source and the image detector.

Moreover, the workstation can reconstruct an X-ray image from the signals of the X-ray image detector 4 for display on a monitor 62. On the other hand, the workstation can also reproduce a patient and exposure list on the monitor, which list contains not only the name of the patient but also the organs or parts of the body to be radiographed. This list can be applied to the workstation 6, for example via a so-called RIS (Radiology Information System) link. There is also provided an input unit 63, for example a keyboard and/or a touch screen unit, for communication with the workstation 6. The patient table 3 (and possibly also the above-mentioned grid wall stand) with the X-ray source 1 and the diaphragm unit 5 are present in a room other than that in which the components 6, 61, 62 and 63 are installed. The examiner is active in both rooms for each X-ray exposure: during the adjustment of the exposure parameters by selection of the organ as well as during the initiation of an X-ray exposure the examiner will be present in one room while he or she will be present in the other room during the positioning of the patient and also during manual adjustment of the diaphragm unit, if any.

The FIGS. 2A to 2E show parts of flow charts which govern the adjustment of the exposure field. In conformity with FIG. 2A, after the selection of an organ or the fetching of APR data, in the step 101 it is checked whether a given flag has been set (M–flag=1) or not (step 102). When the flag has not been set, in the step 103 the workstation generates an instruction for the diaphragm controller 53 so as to adjust the size of the exposure field while taking into account the distance between the X-ray source 1 and the image detector 4 in conformity with the adjustment value stored for the relevant organ to be imaged. However, if the flag has been set, the adjustment remains the same. As is shown in the FIGS. 2B . . . 2E, the flag can be set and reset in dependence on four different events.

Figure 2A:
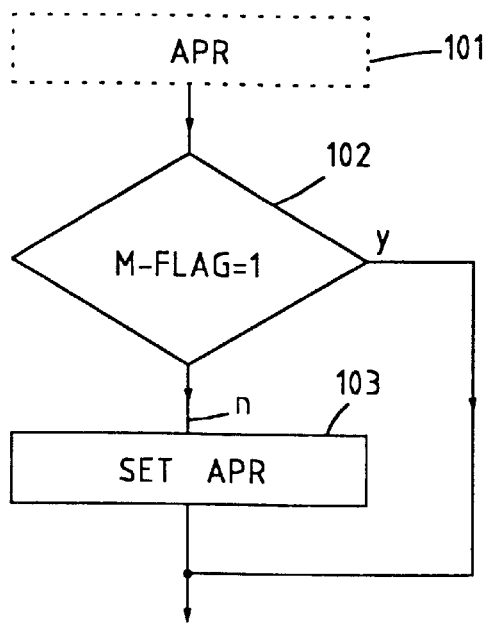
FIGS. 2A–2E show flow charts illustrating the control of the diaphragm unit.
Figure 2B:
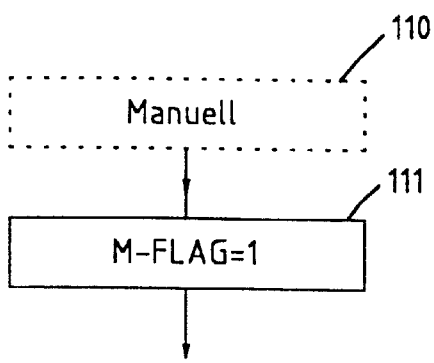
Figure 2C:
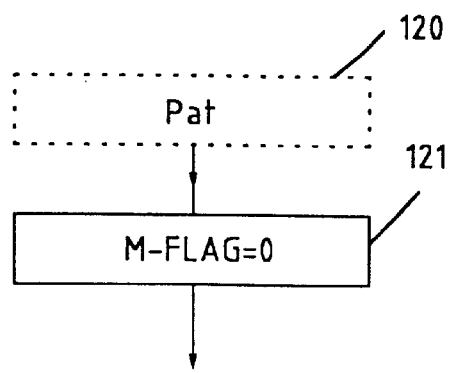
Figure 2D:
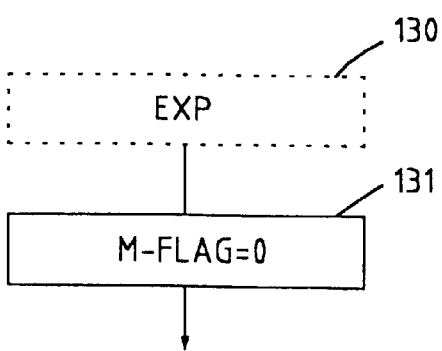
Figure 2E:
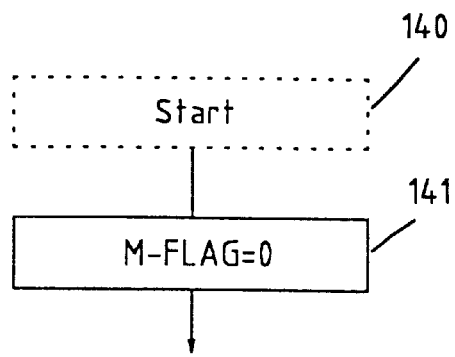

In conformity with FIG. 2B, in the case of manual adjustment of the diaphragm aperture by means of the adjusting member 54 (block 110) the flag is set in the step 111 (M–flag=1). However, in the case of a change of patient (block 120), the flag is reset in the step 121 (M–flag=0, FIG. 2C). The same takes place in the step 131 as shown in FIG. 2D after the initialization of an X-ray exposure (block 130) or in the step 141 upon a (new) start of the system 140.

The operation of the X-ray unit during the execution of a patient and exposure list, reproduced on the monitor 62 by the examiner, will be described in detail hereinafter. It is assumed that the list successively specifies a first exposure in the form of an exposure of the organ 1 (for example, a lateral chest exposure) of the patient A and a second exposure of a second organ of the patient A, for example lung p.a.(even though the lung is to be imaged in both cases, the p.a. and the lateral exposure of this organ are treated as different organs with a different set of exposure parameters). It is assumed that the patient and exposure list specifies as the third exposure an exposure of the same organ (lung p.a.) of a further patient B.

For the first exposure the examiner positions the patient A on the patient table (or in front of said wall stand) and adjusts the size of the exposure field on the diaphragm unit by means of the adjusting member 54, thus setting the flag as shown in FIG. 2B. The examiner subsequently enters the room in which the workstation is located and adjusts the X-ray device for the first exposure, i.e. the exposure of the patient A with the organ 1 is selected, so that an adjustment value for the exposure field is fetched. However, because the flag is set, in conformity with the flow chart shown in FIG. 2A the exposure field is not adjusted to the fetched adjustment value. The examiner then triggers the first X-ray exposure, with the result that (in conformity with FIG. 2D) the flag is reset in conformity with the step 131.

If desired, the patient table may be constructed so that the X-ray source 1 and the image detector 4 are simultaneously displaceable in opposite directions so that slice images can be formed. In such a slice imaging mode usually a series of images of slices in different positions is formed, so that in this mode a (slice) image may not give rise to the described resetting of the flag.

Therefore, when the examiner selects the second exposure on the workstation, in conformity with FIG. 2A the adjustment value for the second organ (lung p.a.) is fetched and adjustment is performed by the diaphragm controller 53 and the motor 52 so that the manual adjustment concerning the previous exposure is overwritten. The examiner then positions the patient A in such a manner that the second exposure can be made. When the adjusting member 54 is then actuated, the preset of the diaphragm unit is changed accordingly by the adjustment value fetched for lung p.a. from the memory 61, so that the flag is set again.

When after this second exposure the third exposure (patient B) in the list is selected in the workstation 3, the flag is reset because of the change of patient (step 121), even if the same organ as during the preceding exposure is to be imaged. The manual adjustments carried out for the second exposure are, therefore, overwritten in conformity with the adjustment value preset for the third organ to be imaged (lung p.a.). If necessary, the examiner can change this preset again by means of the adjusting member 54.

The described routine illustrates that the X-ray device offers the examiner very good economics in combination with high flexibility in respect of adjustment.

All references cited herein are incorporated herein by reference in their entirety and for all purposes to the same extent as if each individual publication or patent or patent application was specifically and individually indicated to be incorporated by reference in its entirety for all purposes.

What is claimed is:

1. An X-ray device comprising:
   an X-ray imaging apparatus,
   an X-ray source,
   an X-ray generator for powering the X-ray source which co-operates with the X-ray imaging apparatus,
   a programmable control system,
   a diaphragm unit which is connected to the X-ray source and includes an adjustable diaphragm aperture in order to preset an exposure field on an X-ray image detection device, the diaphragm aperture being adjustable on the one hand by a drive unit which is controlled by the control system and on the other hand by adjusting means for manual adjustment of the diaphragm aperture, and
   a storage device which co-operates with the control system and in which a respective set of exposure parameters is stored for each of a number of organs, wherein each set includes, in addition to the exposure parameters for the X-ray generator, an adjustment value for adjusting the exposure field, and wherein, when an organ is selected, the adjustment value is fetched and the exposure field is adjusted, by way of the control system and the drive unit, in conformity with the adjustment value associated with the selected organ.

2. An X-ray device as claimed in claim 1, wherein the control system is programmed in such a manner that, after actuation of the adjusting means, the manual adjustment of the exposure field is carried out or preserved independently of an adjustment value fetched before or after that.

3. An X-ray device as claimed in claim 2, wherein the control system is programmed in such a manner that after an X-ray exposure or a change of a patient to be examined an exposure field adjusted by actuation of the adjusting means is adjusted in conformity with the relevant adjustment value fetched.

4. An X-ray device as claimed in claim 1, wherein the distance between the X-ray source and the X-ray image detection device is adjustable, further comprising means for measuring this distance, and wherein the control system is programmed in such a manner that in dependence on the measured distance the diaphragm aperture has a value such that the size of the exposure field on the image detection device assumes its preset value.

5. An X-ray device as claimed in claim 1, wherein X-ray image detection device comprises a flat detector with light-sensitive or X-ray sensitive detector elements which are arranged in the form of a matrix.

* * * * *